United States Patent [19]
Gao et al.

[11] Patent Number: 5,324,860
[45] Date of Patent: Jun. 28, 1994

[54] PROCESS FOR 3,5-DI-TERT-BUTYLSALICYLALDEHYDE

[75] Inventors: Yun Gao, Framingham; Xiaoyi Nie, Worcester, both of Mass.

[73] Assignee: Sepracor, Inc., Marlborough, Mass.

[21] Appl. No.: 144,577

[22] Filed: Oct. 27, 1993

[51] Int. Cl.$^5$ .................... C07C 37/11; C07C 39/06
[52] U.S. Cl. ................................................ 568/476
[58] Field of Search ........................................ 568/436

[56] References Cited

U.S. PATENT DOCUMENTS

| | | | |
|---|---|---|---|
| 3,833,660 | 9/1974 | Smith | 568/436 |
| 3,974,223 | 8/1976 | Cahoy | 568/436 |
| 4,009,210 | 2/1977 | Cahoy | 568/436 |

FOREIGN PATENT DOCUMENTS

| | | | |
|---|---|---|---|
| 829613 | 5/1981 | U.S.S.R. | 568/436 |

OTHER PUBLICATIONS

Duff et al, "J. Chem. Soc.", 1934, pp. 1305–1308.
Duff et al, "J. Chem. Soc.", 1932, p. 1987.
Jacobsen et al. "Highly Enantioselective Epoxidation Catalysts . . . " *J. Am. Chem. Soc.* 113, (1991).
Blazevic et al. "Hexamethylenetetramine, A Versatile Reagent in Organic Synthesis" *Synthesis* 161–176 (1979).
Duff and Furness "A Method for Preparing Secondary Amines and . . . " *J. Chem. Soc.* 1512–1514 (1951).
Casiraghi et al. "Selective Reactions between Phenols and Formaldehydes . . . " *J.C.S.P.*1, 1862–1865 (1980).
Zigeuner and Jellinek, *Monatsh. Chem.* 90, 297–305 (1959).
Komissarova et al. "Anomalous Duff reaction with 2,4-di-tert-butylphenol" *Chem. Abs.* 110:212723c (1988).
Yahagi, Nobuo "Reaction of 2,4-dimethylphenol with hexamethylenetetramine" *Chem. Abs.* 93:8106e (1978).
Zinke et al., *Monatsh. Chem.* 80 148–150 (1949).
Zinke et al., *Monatsh. Chem.* 79 26–41 (1948).
Profft & Krause *Arch. Pharm.* 298, 148–162 (1965).

*Primary Examiner*—Joseph E. Evans
*Attorney, Agent, or Firm*—Heslin & Rothenberg

[57] ABSTRACT

A process for the synthesis of 3-5-tert-butylsalicylaldehyde from 2,4-di-tert-butylphenol and hexamethylenetetramine is disclosed. The reaction provides 3,5-tert-butylsalicylaldehyde in commercially attractive yields from readily available starting materials.

9 Claims, No Drawings

PROCESS FOR 3,5-DI-TERT-BUTYLSALICYLALDEHYDE

FIELD OF THE INVENTION

The invention relates to an improved process for the synthesis of 3,5-di-tert-butylsalicylaldehyde from 2,4-di-tert-butylphenol.

BACKGROUND OF THE INVENTION 3,5-di-tert-butylsalicylaldehyde, I, is a starting material for the preparation of a preferred manganese salen catalyst of formula II [see Jacobsen et al., *J. Am. Chem. Soc.* 113, 7063–7064 (1991)]

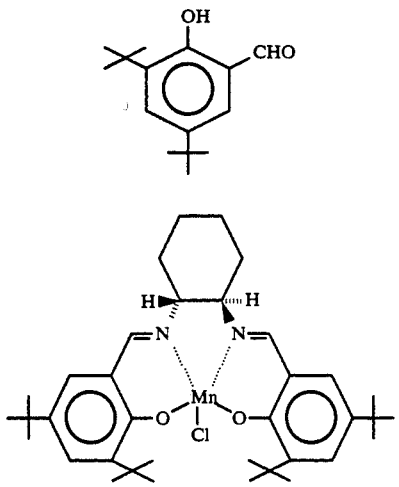

3,5-Di-tert-butylsalicylaldehyde was prepared by Jacobsen et al. by the reaction of 2,4-di-tert-butylphenol with formaldehyde in the presence of SnCl$_4$ and 2,6-lutidine (Casiraghi et al., *J.C.S.P.* 1, 1980, 1862–1865). The use of relatively expensive reagents such as SnCl$_4$ and lutidine, and the production of hazardous wastes make the procedure of Casiraghi unattractive for large-scale synthesis.

It is known that phenols and other activated aromatic compounds can be converted to the corresponding aldehydes by treatment with hexamethylenetetramine (HMT) (formula III).

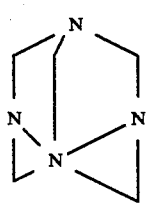

The reaction is known in the art as the Duff reaction; it has been reviewed by Blazevic et al. [*Synthesis*, 1979, 164–167]. The Duff reaction is commonly carried out with HBO$_2$ in dry glycerol, although variations have been reported with trifluoroacetic acid and glacial acetic acid. Unfortunately, although the Duff reaction is usually successful with other activated phenols, it is notoriously poor when the substrate is a 2,4-dialkylphenol. For example, Blazevic et al. (op. cit.) report the formulation of 2-methyl-4-neopentylphenol using glycerol/boric acid in 19% overall yield. When Komissarova et al. attempted formulation of 2,4-di-tert-butylphenol using hexamethylenetetramine in the Duff reaction, they observed that the only product was a dihydro-1,3-benzoxazine [*Chemical Abstracts*, 110: 212723c].

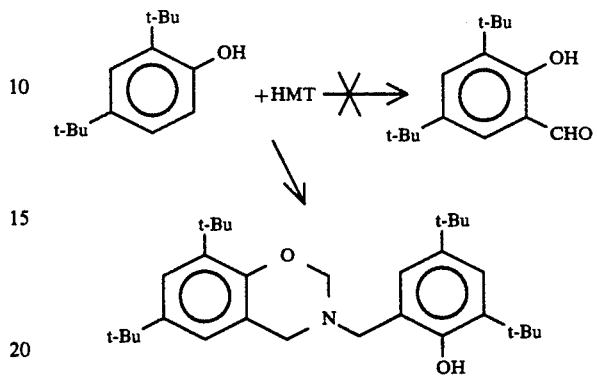

Yahagi reported that the corresponding 1,3-benzoxazine could be prepared very efficiently from 2,4-dimethylphenol and hexamethylenetetramine [*Chemical Abstracts*, 93: 8106e].

Because persons of skill in the art believed that the Duff reaction with HMT and acid was not preparatively useful for dialkyl salicylaldehydes, Zigeuner and Jellinek [*Monatsh. Chem.* 90, 297–305 (1959) p. 299] proposed a different synthetic route. They stated that "On the basis of the oxidative cleavage of the dibenzylamines . . . which proceeds in high yield, a new synthesis of 2-hydroxy-3,5-disubstituted benzaldehydes, which are difficult to prepare by the usual preparative methods, was developed." Their method comprised preparing a dibenzylamine from the reaction of an appropriate phenol with hexamethylenetetramine followed by oxidation of the resulting dibenzylamine to the benzaldehyde using sodium m-nitrobenzenesulfonate in aqueous acetic acid.

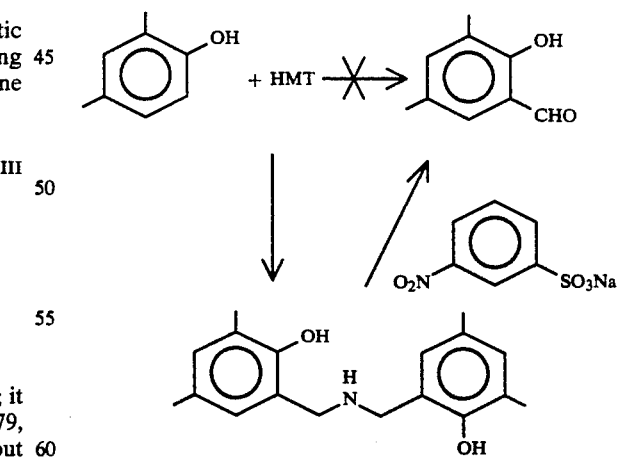

No examples of the direct conversion of 2,4-dialkylphenols to 3,5-dialkylsalicylaldehydes in good yields using hexamethylenetetramine are found in the literature.

It has now been surprisingly found that under a specific set of conditions it is possible to prepare 3,5-di-tert-butylsalicylaldehyde from 2,4-di-tert-butylphenol and hexamethylenetetramine in yields that are feasible for large scale production.

SUMMARY OF THE INVENTION

It is an object of the present invention to provide a commercially attractive method for the preparation of 3,5-di-tert-butylsalicylaldehyde. This object as well as other objects, features and advantages are provided by the following invention, which in one embodiment comprises a process for the preparation of 3,5-di-tert-butylsalicylaldehyde comprising:

(1) heating together 2,4-di-tert-butylphenol and hexamethylenetetramine in glacial acetic acid, followed by (2) adding water or aqueous acid and heating the resulting mixture to produce 3,5-di-tert-butylsalicylaldehyde.

The process is preferably carried out using 0.5 to 2.0 molar solution of 2,4-di-tert-butylphenol and 1–3 equivalents of hexamethylenetetramine in glacial acetic acid at 100° to 130° C. The second step may be carried out either by heating with water or with aqueous acid. A preferred acid is hydrochloric acid or sulfuric acid and in either case the second step is optimally carried out at 100° to 130° C.

A particular embodiment of the process of the invention comprises:

(1) heating a 2M solution of 2,4-di-tert-butylphenol and 2 equivalents of hexamethylenetetramine in glacial acetic acid at about 130° C. for 1 to 5 hours, followed by (2) adding about one volume of water or aqueous acid and heating the resulting mixture at about 130° C. for 0.5 to 1 hour to produce 3,5-di-tert-butylsalicylaldehyde.

Preferred aqueous acids are 4N HCl and 20% $H_2SO_4$ (vol/vol).

DESCRIPTION OF PREFERRED EMBODIMENTS

It has now been found that reaction of 2,4-di-tert-butylphenol with hexamethylenetetramine in glacial acetic acid followed by quenching with water or aqueous acid, extraction with a water insoluble non-polar solvent and filtration through silica gel provides 3,5-di-tert-butylsalicylaldehyde in more than 60% yield and of a purity suitable for the production of chiral Mn-Salen catalysts. Alternatively, reaction of 2,4-di-tert-butylphenol with HMT in glacial acetic acid followed by quenching with an aqueous acid, separating the aqueous phase from the organic phase and recrystallizing the organic phase in methanol provides 3,5-di-tert-butylsalicylaldehyde in more than 40% isolated yield and a purity suitable (>95%) for the production of the catalyst.

In a preferred embodiment of the present invention, one equivalent of 2,4-di-tert-butylphenol is treated with 1 to 3 equivalents, preferably 1.5 to 2 equivalents, of hexamethylenetetramine in glacial acetic acid. The mixture is heated for a period of 1 to 5 hours. The reaction temperature is in the range of 100° to 130° C., preferably about 130° C., and the reaction time is preferably 2 to 3 hours. The concentration of 2,4-di-tert-butylphenol in acetic acid is in the range of 0.5 to 2M, preferably about 2.0M.

After reaction of the 2,4-di-tert-butylphenol and hexamethylenetetramine in glacial acetic acid, the reaction mixture is quenched with water or aqueous acid, preferably with an aqueous acid, in an amount roughly equal to that of the volume of acetic acid used. The aqueous mixture is then further heated at reflux (bath temperature about 130° C.) for a short period of time, preferably 0.5 to 1 hour.

After the treatment with aqueous acid or water, the reaction solution is concentrated under vacuum to recover acetic acid, or it is simply cooled and extracted with a non-polar solvent. Preferred solvents for the extraction are hydrocarbon solvents, such as hexane, heptane, toluene and xylene, or ethers such as diethyl ether and tert-butyl methyl ether.

The crude reaction product is further purified by passing the solution in the non-polar solvent such as hexane or toluene through a pad of silica gel. The solvent is stripped from the filtrate to provide a solid which is suitable for the preparation of Mn-Salen catalyst without further purification.

In another preferred procedure, the reaction solution is cooled to about 55°–65° C. and the organic phase is separated from the aqueous phase. The organic phase is then recrystallized in an alcohol solvent, preferably methanol, to give the salicylaldehyde.

The present invention is more fully illustrated by the following examples:

EXAMPLE 1

A mixture of 10.42 grams (50 mmol) of 2,4-tert-butylphenol and 14.02 grams (100 mmol) of hexamethylenetetramine in 25 mL of acetic acid was heated at 130° C. with stirring for 1 hr. A solution of 12.5 mL of concentrated HCl in 25 mL of water was added and the resulting solution heated at the same temperature for 0.5 hours. After cooling, the solution was extracted with 100 mL of hexane, the hexane phase was washed with 10 mL of water and 10 mL of saturated sodium chloride solution. The hexane solution was filtered through a pad of 10–15 grams of silica gel. The silica gel pad was rinsed with about 300 mL of hexane and the combined hexane solution was concentrated to provide 7.57 grams (64.6% of theory) of 3,5-di-tert butylsalicylaldehyde as a yellow solid.

EXAMPLE 2

A mixture of 10.42 g (50 mmol) of 2,4-di-tert-butylphenol and 21.03 g 150 mmol) of hexamethylenetetramine (HMT) in 50 mL of glacial acetic acid was heated at 130° C. with stirring for 2 hours. Twenty-five mL of water was then added and the resulting mixture was refluxed for 0.5 h. After cooling and workup as in Example 1, 5.5 g of 3,5-di-tert-butylsalicylaldehyde was obtained (46.9% yield).

EXAMPLE 3

A mixture of 208.4 g (1.0 mol) of 2,4-di-tert-butylphenol and 283.2 g (2.0 mol) of HMT in 500 mL of glacial acetic acid was heated at 130 C. with stirring for 2 hours. A solution of 500 mL of 20% (vol/vol) aqueous sulfuric acid was then added and the resulting solution was refluxed for 0.5 hour. The solution was cooled to around 60°–80° C. and the organic phase was separated from the aqueous phase. The organic phase was recrystallized twice from 150–200 mL of cold (0°–5° C.) methanol to give 93 to 107 g (40–46% yield) of pure 3,5-di-tert-butylsalicylaldehyde of greater than 95% purity by HPLC. mp 60°–62° C. $^1$H-NMR (60 MHz, $CDCl_3$): δ9.8 (s,1H); 7.6 (d,1H); 7.3 (d,1H); 1.2–1.5 (d,18H). IR (KBr): 3400, 2980, 1650 $cm^{-1}$.

We claim:

1. A process for the preparation of 3,5-di-tert-butyl-salicylaldehyde comprising:
   (1) heating together 2,4-di-tert-butylphenol and hexamethylenetetramine in glacial acetic acid, followed by
   (2) adding aqueous acid and heating the resulting mixture to produce 3,5-di-tert-butylsalicylaldehyde.

2. A process according to claim 1 wherein a 0.5 to 2.0M solution of 2,4-di-tert-butylphenol and one to three equivalents of hexamethylenetetramine in glacial acetic acid are heated at 100° to 130° C.

3. A process according to claim 1 wherein in step (2) said mixture is heated with an aqueous acid at 100° to 130° C.

4. A process according to claim 3 wherein said aqueous acid is hydrochloric acid or sulfuric acid.

5. A process according to claim 1 comprising:
   (1) heating a 2M solution of 2,4-di-tert-butyl-phenol and 2 equivalents of hexamethylenetetramine in glacial acetic acid at about 130° C. for 1 to 5 hours, followed by
   (2) adding about one volume of an aqueous acid and heating the resulting mixture at about 130° C. for 0.5 to 1 hour to produce 3,5-di-tert-butylsalicylaldehyde.

6. A process according to claim 5 wherein said aqueous acid is 4N HCl or 20% (vol/vol) aqueous $H_2SO_4$.

7. A process for the preparation of 3,5-di-tert-butyl-salicylaldehyde comprising:
   (1) heating together 2,4-di-tert-butylphenol and hexamethylenetetramine in glacial acetic acid, followed by
   (2) adding water and heating the resulting mixture to produce 3,5-di-tert-butylsalicylaldehyde.

8. A process according to claim 7 wherein a 0.5 to 2.0M solution of 2,4-di-tert-butylphenol and one to three equivalents of hexamethylenetetramine in glacial acetic acid are heated at 100° to 130° C.

9. A process according to claim 7 wherein in step (2) said mixture is heated with water at 100° to 130° C.

* * * * *